United States Patent [19]

Williams et al.

[11] 4,041,502
[45] Aug. 9, 1977

[54] SEDIMENTATION RECORDER

[75] Inventors: Raymond H. Williams, Chadwicks; Emil J. Misiaszek, New York Mills, both of N.Y.

[73] Assignee: Williams Tool, Inc., Chadwicks, N.Y.

[21] Appl. No.: 643,088

[22] Filed: Dec. 22, 1975

[51] Int. Cl.² .................... G01D 5/32; G01D 9/30
[52] U.S. Cl. .................. 346/33 A; 73/61.4;
235/151.35; 250/573; 346/49; 356/39
[58] Field of Search .................. 346/33 A, 33 ME, 49;
356/39, 40; 235/151.35; 250/573, 577; 73/290,
293, 61.4

[56] References Cited

U.S. PATENT DOCUMENTS

| 2,104,525 | 1/1938 | Proskouriakoff | 356/40 |
|---|---|---|---|
| 2,982,170 | 5/1961 | Wyss | 356/39 |
| 2,998,291 | 8/1961 | Coggeshall et al. | 346/49 X |
| 3,243,994 | 4/1966 | Erdey et al. | 73/61.4 X |
| 3,300,385 | 1/1967 | Danon | 356/40 X |
| 3,715,761 | 2/1973 | Drekter et al. | 346/33 A |

*Primary Examiner*—Joseph W. Hartary
*Attorney, Agent, or Firm*—Richard H. Smith

[57] ABSTRACT

A sedimentation recorder including an optical tracking head controlled to track the liquid-solid separation boundary in a tube containing a sample of liquid-solid mixture. The tracking head is controlled by a pulse operated servomotor which responds to the output of a photodetector mounted in the tracking head. A two-pen plotter is provided to record the sedimentation behavior of the sample. One pen is connected to the tracking head and continuously records the position of the liquid-solid separation boundary to provide a settling curve. The other pen is driven by a rate of change mechanism and records the approximate rate of change of the separation boundary position. The rate of change mechanism operates by measuring the excursion of the tracking head during each of a series of successive time intervals. The difference between each excursion measurement and the preceding measurement is calculated and each difference value is converted into a corresponding number of pulses. The pulses are applied to drive a second pulse operated stepping motor which in turn drives the rate of change recording pen.

6 Claims, 4 Drawing Figures

SEDIMENTATION RECORDER

BACKGROUND OF THE INVENTION

This invention relates to the measuring and recording of the settling behavior of certain liquid-solid mixtures and, more particularly, relates to the automatic recordation of sedimentation phenomena in blood samples.

Heretofore observation of sedimentation phenomena blood samples has been carried out basically through two techniques known as the Wintrobe method and the Westergren method. These techniques involve the manual observation and recordation of the settling behavior of the red cells of a blood sample contained in a glass tube of standardized dimensions. As the red cells settle out, the separation boundary between the cells and the clear plasma fluid is observed against a calibrated scale provided on or adjacent to the tube. One or two readings are manually taken as settling progresses over a one to two hour period. According to the usual procedure, a first reading is taken after one hour and a second after two hours, the latter in most cases representing the maximum settling point of the sample.

These procedures provide only a small amount of insight into the settling phenomena as they record only two widely spaced points on the curve. They are further subject to the inaccuracies inherent in human observation and measurement.

Of the automatic sedimentation recorders devised to date none have provided a highly accurate, continuous record of the settling process from beginning to end. A typical technique used for automatic recording has been to direct an image of the settling tube onto a moving sheet of photosensitive paper. The solid-liquid separation boundary within the tube traces a line on the paper which, on development, gives a visible display of the settling phenomena. A drawback of this system is that photosensitive paper is expensive and difficult to work with and requires the use of complex light-tight enclosures as well as a separate development step at the end of the process. Further, it is difficult to obtain a crisp, well defined settling trace with this type of photographic system.

OBJECTS AND SUMMARY OF THE INVENTION

It is therefore a principal object of the present invention to provide an improved sedimentation recorder that gives a highly accurate, well defined, continuous recording of sedimentation phenomena.

A further object is to provide an improved recorder of the type described that records sedimentation phenomena on ordinary plotting paper.

Still a further object is to provide a recorder of the type described that provides a record of the approximate rate of change of the settling curve as well as a record of the settling curve itself.

To achieve the foregoing objects and in accordance with the purpose of the invention, as embodied and broadly described herein, the sedimentation rate measuring device of the invention comprises a transparent tube containing a liquid-solid mixture, a movable carriage supported adjacent to the tube and arranged to move in a path parallel thereto, and irradiation means, which may be mounted on said carriage, for directing a beam of radiation through the tube. In addition, the invention contemplates the use of photodetection means mounted in a position to detect the beam of radiation and which is further adapted to generate an output signal indicating the intensity of the detected radiation, a motor for driving the carriage control, means responsive to the photodetection means for activating the motor to drive the carriage in a predetermined direction when the output signal exceeds a predetermined level such that the carriage is caused to track the liquid-solid separation boundary within the tube, means for registering the duration of each time interval during which the motor is activated and means responsive to the last-mentioned means for indicating the rate of change of the position of the separation boundary within the tube.

In further accordance with the purpose of the invention pursuant to a second aspect thereof, and as embodied and broadly described herein, the sedimentation recorder and rate measuring device of the invention comprises optical sensing means movably mounted adjacent the tube containing solid particles suspended in a liquid medium whereupon the optical sensing means is constructed and arranged to generate an output signal when positioned in alignment with the liquid-solid separation boundary in the tube, a servo motor controlled by the output signal to drive the sensing means to following movement of the liquid-solid separation boundary as settling occurs, measuring means for measuring the excursion of the servo motor during each of a series of consecutive time intervals and difference means for calculating the difference between each successive pair of excursion measurements made by the measuring means. In addition, recording means are provided for recording the difference value derived by the difference means during each time interval whereby the approximate rate of change of the position of the separation boundary within the tube is recorded.

In accordance with still a third aspect of the invention, as embodied and broadly described herein, the sedimentation recorder comprises a transparent tube containing a liquid-solid mixture, a movable carriage supported adjacent to the tube and arranged to move in a path parallel thereto, irradiation means, which may be mounted on the carriage, arranged to direct a beam of radiation through the tube, photodetection means, which also may be mounted on the carriage, located in a position to detect the beam of radiation, the photodetection means being further adapted to generate an output signal indicating the intensity of the detected radiation, a motor for driving the carriage, a motor drive circuit and a coincidence circuit having a first and second input connected to the motor drive circuit.

In further accordance with this aspect of the invention, there is provided a threshold circuit connected to receive the output signal from the photodetection means and adapted to feed a first control signal to the first input of the coincidence circuit when the photodetector output exceeds a predetermined level, means for supplying a second control signal to the second input of the coincidence circuit whereby the latter operates to energize the motor in response to outputs from the threshold circuit such that the carriage is caused to track the liquid-solid separation boundary within the tube and recording means for generating a record of the motion of the motor thus producing a record of the settling of the solids within the liquid-solid mixture.

In accordance with still a third aspect of the invention, as embodied and broadly described herein, the sedimentation recorder comprises a transparent tube containing a liquid-solid mixture, a movable carriage supported adjacent to the tube and arranged to move in a path parallel thereto, irradiation means, which may be mounted on the carriage, arranged to direct a beam of radiation through the tube, photodetection means, which also may be mounted on the carriage, located in a position to detect the beam of radiation, the photodetection means being further adapted to generate an output signal indicating the intensity of the detected radiation, a motor for driving the carriage, a motor drive circuit and a coincidence circuit having a first and second input and an output connected to the motor drive circuit.

In further accordance with this aspect of the invention, there is provided a threshold circuit connected to receive the output signal from the photodetection means and adapted to feed a first control signal to the first input of the coincidence circuit when the photodetector output exceeds a predetermined level, means for supplying a second control signal to the second input of the coincidence circuit whereby the latter operates to energize the motor in response to outputs from the threshold circuit such that the carriage is caused to track the liquid-solid separation boundary within the tube and recording means for generating a record of the motion of the motor thus producing a record of the settling of the solid within the liquid-solid mixture.

These and other objects, features and advantages of the invention will be made apparent from the following detailed description of a preferred embodiment of the invention, the description being supplemented by drawings as follows.

DETAILED DESCRIPTION OF EMBODIMENT

Figure 1:
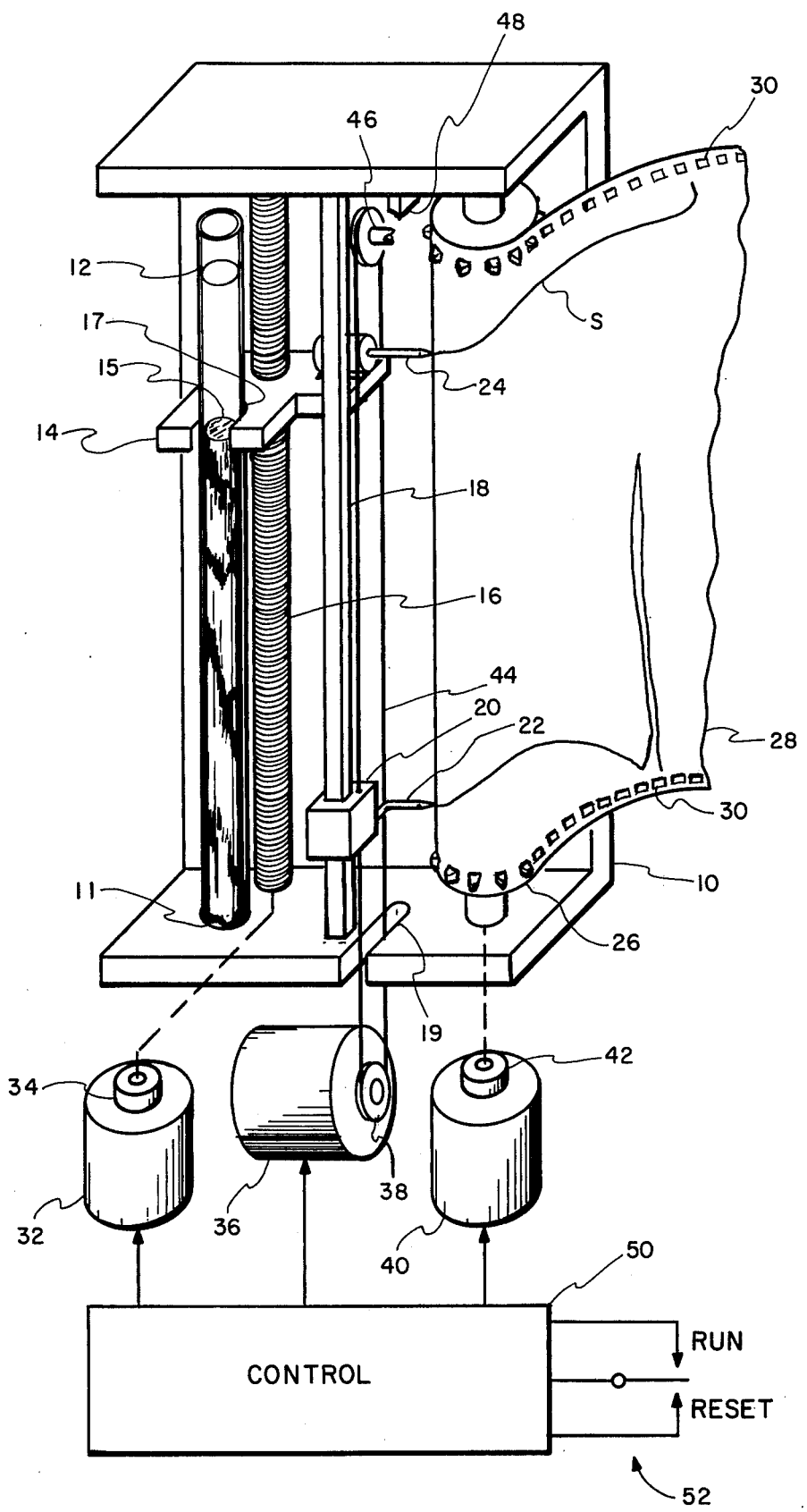
FIG. 1 is a mechanical schematic illustrating the basic features of a preferred embodiment of a sedimentation recorder constructed in accordance with the invention.

Referring to FIG. 1, a glass tube 12 containing a sample of blood is supported in the base of recorder frame member 10. A recess or socket 11 provided in the base of the frame holds the tube 12 in a rigid, vertical position and clamps the tube tightly enough to prevent swaying or vibration that would disturb the sample or the measurement process. A tracking head 14 is disposed immediately adjacent the sample tube and is supported on a drive screw 16 adapted to move the head up and down in a path parallel to the tube. A guide finger (not shown) extending out from the rear of head 14 rides in a vertical groove in the back of frame 10 so that rotation of the screw 16 is not coupled to the head. A notch 17 is provided in the head 14 such that portions of the head protrude on either side of the tube. Irradiation means such as a light emitting diode (LED) are included in the left portion of the head and photodetection means such as a photodiode are provided on the opposite side of the tube in the right portion of the head.

A drive motor 32 is mounted below the base of frame 10 and is coupled through gear reduction means 34 to the drive screw 16. A servo circuit in the control circuit 50 generates a control signal which energizes motor 32, causing the drive screw 16 to move head 14 such that the beam of radiation passing between the LED and the photodiode stays in alignment with the separation boundary 15 between the red cells and the clear plasma fluid in the blood sample.

The settling process is graphically recorded as a curve S inscribed by a pen 24 mounted on the tracking head 14 as the pen moves over a sheet of plotting paper 28. The latter is trained over a rotating drum 26. Drum 26 is driven at a constant speed by a motor 40 through suitable gearing 42. Sprocket pins at the top and bottom of the drum register with sprocket perforations 30 in the paper and serve to keep the paper properly aligned on the drum and moving at a constant speed.

A square guide rail 18 extending between the top and bottom portions of frame 10 serves to guide the movement of a carriage member 20 which supports a second recording pen 22. Carriage 20 is driven by a motor 36 via a wire 44 which is tightly trained over a pair of pulleys 38 and 46, the former being mounted on the drive shaft of motor 36. Pulley 46 is rotatably supported on an arm 48 extending out from the top of frame 10. Arm 48 is cut away in FIG. 1 to more clearly show the pulley.

Carriage 20 and tracking head 14 are arranged so that they are both free to travel substantially the full distance between the top and bottom portions of the frame. Pens 22 and 24 are slightly offset so that they do not interfere as they pass one another, pen 22 passing approximately one-eighth of an inch in front of pen 24. Wire 44 is connected to the top and bottom surfaces of carriage 20 and the rear-most portion of the wire passes just behind head 14. A slot 19 is provided in the base of frame 10 to permit free movement of the wire as it is driven over the pulleys. Pen 22 inscribes a curve R on the plotting paper 28 which represents the approximate rate of change of the settling curve S.

Figure 2:
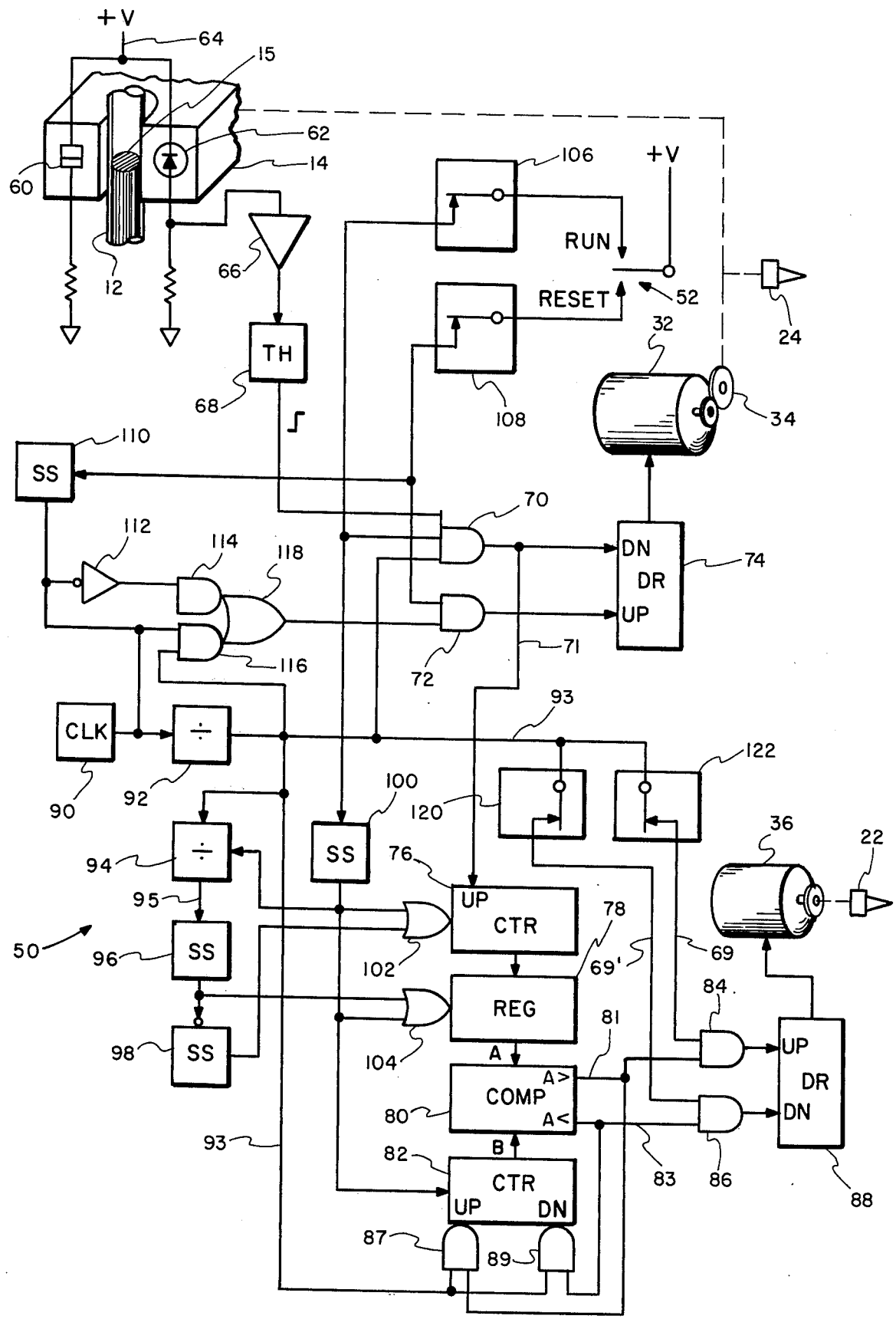
FIG. 2 is a schematic circuit diagram showing the control circuits represented by the "control" block of FIG. 1.

FIG. 2 illustrates the control circuits 50. An LED 60 is mounted in the left portion of tracking head 14 and continuously irradiates a photodiode 62 through the tube 12. The output from the photodiode circuit is a continuous voltage signal representing the intensity of radiation passing through the tube, as detected at the photodiode. An amplifier 66 presents the photodiode output to a threshold circuit 68. The latter may comprise, for example, a comparator amplifier which compares the level of the photodiode output signal against a predetermined threshold level and generates a high logic-level output when the photodiode output signal is above the threshold level. When the photodiode output is below the threshold the circuit 68 generates a low logic-level output.

An AND circuit 70 receives the output from threshold circuit 68 along with two other signals, one from RUN-RESET switch 52 and the other from a frequency driver circuit 92 via line 93. AND 70 generates an output which activates motor drive circuit 74 when all three inputs are at the high level.

A master clock circuit 90 produces a continuous squarewave output signal at, for example, 136 Hz. for timing the operation of the system. Frequency divider circuits 92 and 94 step the 136 Hz. signal down to 68 Hz. and 0.0664 Hz. signals, respectively. Circuits 92 and 94 may comprise, for example, a one-stage binary counter circuit and a ten-stage binary counter circuit, respectively. The former divides in 136 Hz. input signal in half, resulting in a 68 Hz. squarewave output and the latter divides its 68 Hz. input signal in half ten times resulting in a 0.0664 Hz. squarewave output. Positive-going transitions occurs in th latter signal at approximately 15 second intervals.

Motor 32 is a pulse operated stepping motor such as a "Sigma" series 18 bi-directional, two phase permanent magnet motor. When switch 52 is set in its upper "RUN" position, AND 70 feeds a 68 Hz. pulse train to driver circuit 74 so long as a high level signal is being generated by the threshold circuit 68. This causes driver 74 to feed a 68 Hz. pulse train to motor 34, causing the latter to rotate in a smooth, continuous motion to drive the carriage 14 and pen 24 in a downward direction. The gear train 34 together with the pitch of drive screw 16 represent a very high gear ratio such that one revolution of the motor produces only approximately 0.0025 inch of downward motion of head 14.

The tracking head 14, threshold circuit 68, AND gate 70, driver circuit 74 and motor 32 together form a position servo loop. So long as head 14 is aligned such that the beam of radiation from LED 60 passes through an empty portion of glass tube 12 or through the clear plasma fluid on the top portion of the settling mixture, threshold circuit 68 activates AND 70 so that the 68 Hz. clock signal applied to driver circuit 74 causes motor 32 to drive the tracking head downward. When the head moves the alignment with the liquid-solid separation boundary 15, the relatively opaque mass of blood cells in the tube begins to occlude the beam of radiation and this reduces the level of the photodiode output signal. When the signal level falls below the predetermined threshold, AND gate 70 is deactivated. This cuts off the motor drive pulses and the tracking head 14 comes to rest. Due to the extremely high gear ratio between the motor 32 and head 14 the latter follows the gradual downward motion of the separation boundary 15 in an essentially continuous, extremely close and accurate tracking motion that produces a very accurate representation of the settling phenomena via the curve S which is inscribed by pen 24.

A limit switch 106 is provided in the circuit between switch 52 and AND gate 70. The actuator of the limit switch is placed in the path of tracking head 14 at its lowest point of permissible travel. Switch 106 is a safety device for turning off motor 32 when head 14 reaches its lower limit of travel in the event an operator turns the apparatus on when there is an empty tube (or no tube at all) in socket 11. When the switch opens, the center input to AND 70 shifts low and prevents any further clock pulses from passing to driver circuit 74.

The rate of change plotting mechanism includes a digital counter circuit 76, a storage register 78, a second digital counter 82 and a digital comparator circuit 80. Pulses generated by AND 70 to operate the tracking motor 34 are presented to the "up" input of counter 76 via line 71, each pulse incrementing the counter by one count. After each interval of approximately 15 seconds, a single-shot multivibrator circuit 96 connected to receive the 0.0664 Hz. squarewave signal from frequency divider 94, generates a sampling pulse. This pulse is fed to register 78 through an OR circuit 104 and causes the register to store a number corresponding to the digital count then present in counter 76. When the pulse from single-shot 96 terminates, a trailing-edge responsive single-shot 98 generates a reset pulse which is fed to the reset input of counter 76 through an OR circuit 102. This restores counter 76 to zero whereupon it begins to accumulate a new count of motor drive pulses. Counter 76 is constructed so that when it reaches a maximum count, e.g. 1000, during a given count cycle, it stops counting and holds the maximum count value until the reset pulse is received via OR 102.

However, the count transferred into register 78 is presented to the A input of comparator 80 and is compared against the count presented to the B input of the comparator from counter 82. If the two counts are the same no output issues from the comparator. If the A count is larger, an output signal is generated on "A>" output line 81. This signal conditions AND circuit 84 and the latter passes the 68 Hz. squarewave signal on line 69 to the "up" input of motor drive circuit 88. This causes motor 36, which is a pulse operated DC stepping motor similar to the motor 32, to drive the rate of change recording pen 22 in an upward direction.

If the count presented to comparator input A is smaller than that appearing at input B, an output signal is generated on "A<" output line 83. This signal conditions AND 86 and the latter passes the 68 Hz. squarewave signal on line 69' to the "down" input of motor drive circuit 88, causing the motor 36 to drive the pen 22 in a downward direction.

The "A<" and "A>" outputs from the comparator are also fed to a second pair of AND gates 87 and 89 which are connected to the "up" and "down" inputs, respectively, of the counter 82. The 68 Hz. clock signal is applied to the second input of each of the AND's via line 93. Each time an output is generated by comparator 80 one of the ANDs 87 or 89 feeds the pulses to its respective counter input whereby each pulse steps the counter by one count up or down. Thus each time a new count is transferred into register 78 from counter 76, counter 82 is driven up or down until its count equals that in register 78. When the counts are equal, AND gates 84/86 and 87/89 are deconditioned and the stepping operation terminates. Motor 36 is thus driven through a distance corresponding to the number of pulses presented to counter 82 during each cycle (unless the pen reaches its upper limit prior to termination of the count, a condition to be described subsequently). Pen 22 thus records the difference between successive counts presented to register 78. If a given count is larger than the preceding count the pen 22 moves upward by the difference value. If the count is smaller than the preceding count the pen moves downward by the difference value. The curve inscribed by the pen thus represents the approximate rate of change of the settling curve plotted by pen 24.

A pair of limit switches 122 and 120 are provided lines 69 and 69' respectively which feeds AND circuits 84 and 86. The actuators for these switches are positioned in the path of travel of carriage 20 with switch 122 defining the upper travel limit and switch 120 defining the lower limit. These switches prevent the carriage 20 from being overdriven. Upper switch 122 also functions as part of the "zeroing" system for pen 22, as will be described subsequently.

Reset means are provided for permitting the tracking head 14 to be rapidly returned to a predetermined starting position near the top of drive screw 16. "RUN-RESET" switch 52 has an upper position for placing the system into its normal operating condition. The lower position of switch 52 is the reset position and when in that state the switch removes the bias input from AND 70 and applies a bias signal to an AND circuit 72. The latter supplies control pulses to the "up" input of motor drive circuit 74.

When the switch is first moved to the reset position, a single-shot multivibrator 110 is triggered and feeds an output pulse of predetermined duration to an AND gate 116 and to an inverter 112. AND 116 is thus conditioned and passes the 68 Hz. clock signal from frequency divider 92 to AND 72 through an OR circuit 118. This energizes motor 32 to drive the tracking head 14 upwardly at the same slow that is used under tracking conditions. Once the static inertia of the motor and its load has been overcome, single-shot 110 times out and AND 116 blocks further passage of the 68 Hz. pulses. However, at the same instant inverter 112 energizes AND 114 and causes the basic 136 Hz. pulses from clock 90 to pass to AND 72 through OR 118. This drives the motor at twice its normal speed and causes it to return to its starting position at an accelerated rate.

Figure 4:
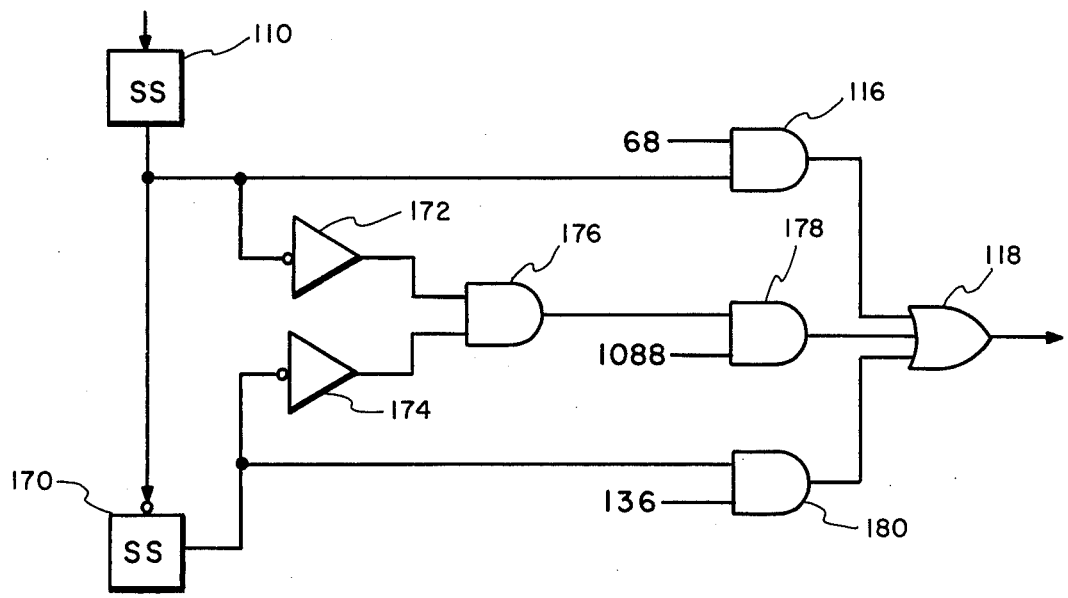
FIG. 4 is a schematic circuit diagram showing an alternate form of reset pulse generating circuit that may be used in the circuit system of FIG. 2.

If desired, an even higher frequency output may be provided from clock 90 to return the tracking head even faster. A circuit for accelerating the motor up to a 1088 Hz. pulse rate is shown in FIG. 4. Single-shot 110, AND gate 116 and Or 118 perform the same function as in the FIG. 2 circuit. That is, single-shot 110 is triggered when switch 52 is thrown to "reset" so that 68 Hz. pulses are applied to the motor through AND 116 and OR 118. However, when single-shot 110 times out, a trailing edge responsive single-shot 170 produces a timed pulse at its output and this conditions an AND 180. This gates 136 Hz. pulses to OR 118 whereupon the speed of the motor is increased. After the motor accelerates to the 136 Hz. pulse rate velocity, single-shot 170 times out and this energizes an AND circuit 176 which is connected to the outputs of both single-shots through a pair of inverters 172 and 174. AND 176 in turn conditions AND gate 178 which feeds 1088 Hz. clock pulses to the motor so that the motor drives the tracking head back to its starting position at a rapid rate. To operate in this fashion clock 90 is modified so that its primary output frequency is 1088 Hz. An additional 3-stage frequency divider is provided to count the 1088 Hz. signal down to the 136 Hz. pulse rate which is supplied to divider 92.

Referring back to FIG. 2, when the head 14 reaches its starting position, a limit switch 108, which is positioned in the path of the head near its upper limit of travel, opens and deconditions AND 72, terminating the reset operation. The motor thus stops and the head is in position to begin operation on a new blood sample. When switch 52 is placed in the "RUN" position to begin the operation, a single-shot multivibrator 100 is triggered to produce a pulse which resets the rate of change calculation circuits. The pulse from single-shot 100 is fed to the reset inputs of counters 76 and 82 and simultaneously restores their respective counts to zero. The same pulse actuates register 78 through OR 104 so that when counter 76 goes to zero the register 78 is also zeroed. The single-shot output also resets the counter stages in frequency divider 94 so that the first timing period will be a full 15 second interval.

OPERATION

Figure 3:
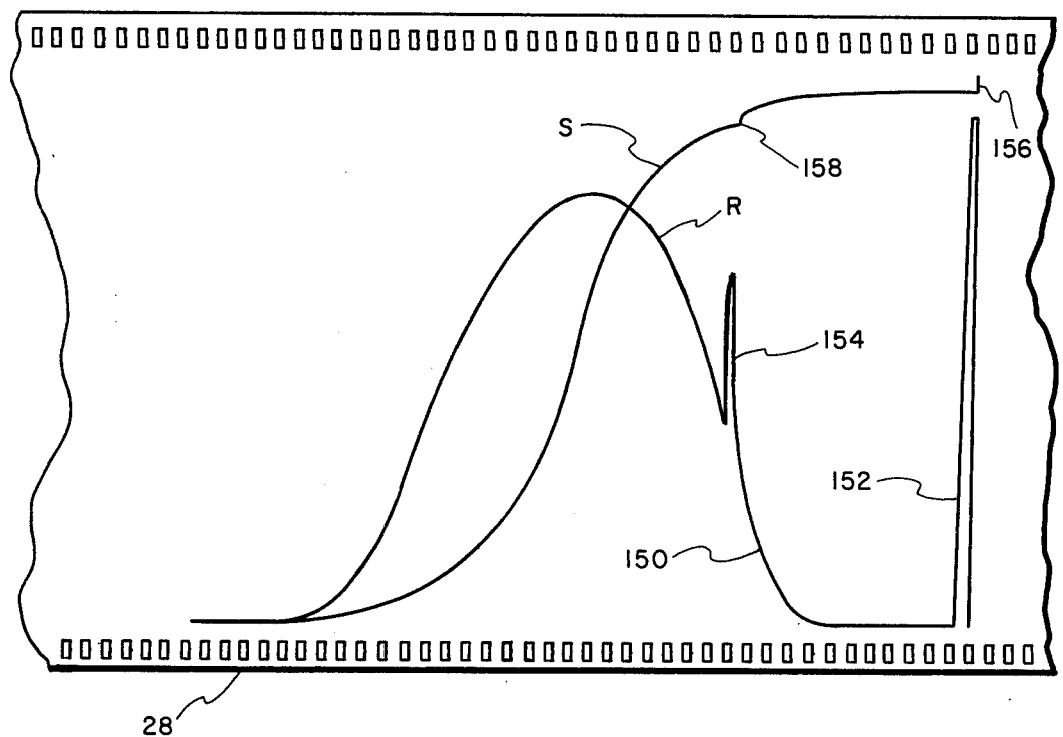
FIG. 3 is a diagram illustrating a typical plot of the settling curve and the rate of change curve as generated by the system of FIGS. 1 and 2.

Referring to FIGS. 1, 2 and 3, operation of the above described preferred embodiment is hereinafter set forth.

Prior to placing the tube 12 containing the sample to be tested in the recorder, the operator first places switch 52 into the "RESET" position to restore the tracking head 14 to its proper starting point. After the sample tube 12 has been properly prepared the operator places it into socket 11 in the base of the recorder frame 10 (FIG. 1). The level of the blood sample should come to a point slightly the (e.g., ⅛ to ¼ inch) the tracking head 14. The operator throws switch 52 to "RUN" and thereafter is free to pursue other duties. Operation of the recorder from this point is totally automatic Initially, the photodiode 62 (FIG. 2) generates a high level output signal because the beam from LED 60 passes through the empty upper portion of the glass tube 12. This causes motor 32 to drive the head downward at its maximum rate of travel. This produces an almost vertical line 156 at the beginning of the settling curve S (FIG. 3). When the head comes into alignment with the relatively opaque blood sample, the photodiode output signal drops below the threshold level set by circuit 68 and turns the motor 32 off. This stops the tracking head at a point in registration with the uppermost distribution of red cells in the sample. The initial excursion of the head takes only a few seconds.

After 15 seconds have elapsed, the count in counter 76 is transferred into register 78 and operation of the rate of change circuits is initiated. In most cases, the count that was accumulated during the initial excursion of the tracking head more than exceeds the amount of pulses needed to drive the rate of change carriage 20 from its bottom limit to its top limit position. This number may be, for example, 1000 pulses. Counter 76 will thus have been driven to 1000 and held at that level. Of course, since counter 82 was previously reset by single-shot 100 its output is at zero.

Comparator 80 thus produces an output on line 81 and this output conditions ANDS 84 and 87 whereby pen 22 is driven upwardly and clock pulses are applied to the "up" input of counter 82 until it reaches a count of 1000. If carriage 20 reaches its upper travel limit before counter 82 reaches a count of 1000 (the carriage may not have been at is lower limit at the start of operation), limit switch 122 opens to halt the carriage at its upper limit. This initial maximum excursion of the rate pen 22 is shown in FIG. 3 by the "spike" 152 in the rate curve R.

After the next 15 second interval has elapsed, the count transferred to register 78 is zero (or very low) since the amount of red cell settling in that period will have been negligible. This means that the B input to comparator 80, which input is sitting at 1000, causes a comparator output to appear on line 83 which activates ANDs 86 and 89 and causes the rate pen to drop back to its zero position and causes counter 82 to decrement down to the level of the zero count stored in register 78. This accounts for the negative-going portion of "spike" 152 shown in FIG. 3.

The remaining portions of the settling curve S and the rate of change curve R are inscribed as shown in FIG. 3 by repetitive operation of the system in the manner described above. It can be appreciated that each count entered into register 78 during this operation of the system represents the duration of the time interval that motor 32 was activated on its immediately preceding excursion cycle. The rate curve R has a somewhat "stepped" appearance which, for simplicity, has not been attempted in the graphic depiction of FIG. 3. The second spike 154 shown in the rate curve often appears in a typical recording and is a settling phenomenon caused by sudden separation of the concave meniscus of the plasma and the convex meniscus of the red cell portion of the mixture. This occurrence causes only a very slight, sometimes imperceptible, shift in settling curve S as shown at 158. The rate curve, however, always reveals this phenomenon quite clearly.

The total time required to complete the settling trace is usually between 1 and 4 hours. It is thus important that the system be capable of unattended operation since it is often desirable to process samples at off-hours such as overnight. For this reason it may be advantageous to include a manually settable multi-hour timer in the main power supply circuit to the recorder so that the LED circuit as well as paper drive motor 40 are automatically turned off when the trace has been completed.

In order to start the recorder to process a new sample the operator simply inserts a new sample tube, throws switch 52 to "reset" until the tracking head has returned to its start position and then throws the switch to "run".

Thus summarizing the description of the invention as hereinabove provided there has been described a sedimentation rate measuring device comprising a transparent tube containing a liquid-solid mixture, a movable carriage supported adjacent to the tube and arranged to move in a path parallel thereto, irradiation means (which may be mounted on the carriage) for directing a beam of radiation through the tube, photodetection means (which also may be mounted on the carriage) provided in a position to detect the beam of radiation, the photodetection means being further adapted to generate an output signal indicating the intensity of the detected radiation, and a motor for driving the carriage.

Furthermore, the invention hereinabove described includes control means responsive to the photodetection means for activating the motor to drive the carriage in a predetermined direction when the output signal exceeds a predetermined level such that the carriage is caused to track the liquid-solid separation boundary within the tube. As illustrative of such control means, the exemplary embodiment hereinabove described provides a threshold circuit 68, a coincidence circuit 70 and a motor drive circuit 74, all illustrated in FIG. 2.

In addition, a further aspect of the invention contemplates the use of means for registering the duration of each time interval during which the motor is activated (such duration in the case of the described embodiment also representing measurement of the distance of motion generated by the motor during such time interval) and means responsive to the registering means for indicating the rate of change of the position of the separation boundary within the tube. As illustrated in the exemplary embodiment described hereinabove, the registering means includes counter 76 and register 78, shown in FIG. 2, which are arranged to generate and store a representation of the length of each time interval during which the motor is activated. As further exemplified in the embodiment hereinabove described, the rate of change indicating means includes the comparator 80, counter 82, AND circuits 84 and 86, motor drive circuit 88 and motor 36, which operates in response to the output of drive circuit 88 to move a pen to record an indication of the rate of change of the position of the liquid-solid separation boundary.

It will be appreciated that various changes in the form and details of the above described preferred embodiment may be effected by persons of ordinary skill without departing from the true spirit and scope of the invention.

We claim:

1. In a sedimentation recorder the combination comprising:

a transparent tube containing a liquid-solid mixture;
   a movable carrriage supported adjacent to said tube and arranged to move in a path parallel thereto;
   irradiation means arranged to direct a beam of radiation through said tube;
   photodetection means mounted on said carriage in a position to detect said beam of radiation, said photodetection means being further adapted to generate an output signal indicating the intensity of said detected radiation;
   a motor for driving said carriage;
   a motor drive circuit;
   a coincidence circuit having a first and second input and an output connected to said motor drive circuit;
   a threshold circuit connected to receive said output signal from said photodetection means and adapted to feed a first control signal to the first input of said coincidence circuit when said photodetector output exceeds a predetermined level;
   means for supplying a second control signal to the second input of said coincidence circuit whereby the latter operates to energize said motor in response to outputs from said threshold circuit such that said carriage is caused to track the liquid-solid separation boundary within said tube; and
   recording means for generating a record of the motion of said motor thus producing a record of the settling of the solids within said liquid-solid mixture.

2. The combination set forth in claim 1 wherein said motor comprises a pulse-operated stepping motor and said means for supplying said second control signal comprises a pulse generator adapted to supply pulses at a frequency sufficient to produce smooth, continuous motion of said stepping motor.

3. In a sedimentation recorder for measuring the settling rate of solid particles suspended in a liquid medium contained in a transparent tube, the combination comprising:

optical sensing means movably adjacent said tube and constructed and arranged to generate an output signal when positioned in alignment with the liquid-solid separation boundary with said tube;
   a servo motor controlled by said output signal to drive said sensing means to follow movement of said liquid-solid separation boundary as settling occurs;
   measuring means for measuring the excursion of said servo motor during each of a series of consecutive time intervals;
   difference means for calculating the difference between each successive pair of excursion measurements made by said measuring means; and
   recording means for recording the difference value derived by said difference means during each said time interval whereby the approximate rate of change of the position of said separation boundary within said tube is recorded.

4. The combination set forth in claim 3 wherein said servo motor comprises a pulse operated stepping motor and wherein said measuring means comprises:
   means for counting the number of pulses supplied to said servo motor during each said time interval and for supplying a signal representing said count to said difference means at the termination of each interval.

5. The combination set forth in claim 4 wherein said difference means comprises:

storage means for storing the count supplied by said counting means after each said time interval;

means for supplying a source of pulses;

a reversible counter;

gating means for applying said pulses to said reversible counter to cause the latter to increment; and comparing means for comparing the count stored in said storage means with the count of said reversible counter and for supplying an output to control said gating means in response to the difference therebetween whereby a number of pulses is produced at the output of said gating means corresponding to the difference value between said counts during each said time interval.

6. The combination set forth in claim 5 wherein said recording means comprises:

a graphic plotting device including marking means for inscribing a line on a moving record medium;

a second pulse operated stepping motor arranged to drive said marking means; and drive means for receiving the pulses produced by said gating means for applying corresponding drive pulses to said second motor whereby said marking device records on said record medium the consecutive difference values generated by said difference means.

* * * * *